(12) United States Patent
Hillier et al.

(10) Patent No.: US 8,544,497 B2
(45) Date of Patent: Oct. 1, 2013

(54) FLUID TRANSFER DEVICE AND SYSTEM

(75) Inventors: Brian Hillier, Billerica, MA (US);
Martin Szyk, Billerica, MA (US);
Aaron Burke, Billerica, MA (US);
Joseph Almasian, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 158 days.

(21) Appl. No.: 12/902,430

(22) Filed: Oct. 12, 2010

(65) Prior Publication Data

US 2011/0253233 A1    Oct. 20, 2011

Related U.S. Application Data

(60) Provisional application No. 61/280,172, filed on Oct. 30, 2009.

(51) Int. Cl.
*F16K 15/00* (2006.01)
*F16K 31/00* (2006.01)

(52) U.S. Cl.
USPC .......................... 137/542; 251/297; 251/344

(58) Field of Classification Search
USPC ................ 239/441, 423, 424, 583; 137/550, 137/549, 544; 251/149.9, 344, 297, 284, 251/259
See application file for complete search history.

(56) References Cited

U.S. PATENT DOCUMENTS

| 214,367 | A | 4/1879 | Colvin |
| 988,378 | A | 4/1911 | Olson |
| 1,503,132 | A | 7/1924 | Prator |
| 1,585,163 | A | 5/1926 | Milner |

(Continued)

FOREIGN PATENT DOCUMENTS

| CN | 101022875 A | 8/2007 |
| DE | 2161702 | 6/1973 |

(Continued)

OTHER PUBLICATIONS

Gore's Third Supplemental Response to Millipore's First Set of Interrogatories [Interrogatory No. 11], Civil Action No. 11-346-SLR, United States District Court for the District of Delaware, dated Dec. 21, 2011, part 1—pp. 1-43; part 2—pp. 44-85 with Exhibits A-E (334 pages), Exhibits F-G (115 pages) and Exhibits H-I (114 pages).

(Continued)

*Primary Examiner* — Eric Keasel
*Assistant Examiner* — Kevin Barss
(74) *Attorney, Agent, or Firm* — Nields, Lemack & Frame, LLC

(57) ABSTRACT

Fluid transfer apparatus including a body having a bore formed through at least a portion of its interior. Contained within the bore is a movable plunger that moves without changing the axial dimensions of the body. A first end of the body contains a face designed to be attached to an upstream component. A second end of the body is connected to a downstream component such as a filter, pipeline, etc. A first end of the plunger, when it is in the closed position, is in alignment with the face of the body, which combined form a steamable surface and a sterile barrier against the environment to the remainder of the interior of the body, the plunger and downstream components. An outer annular collar is rotatable relative to the body and causes the plunger to move axially within the bore from an open to a closed position.

12 Claims, 8 Drawing Sheets

(56) References Cited

U.S. PATENT DOCUMENTS

| | | |
|---|---|---|
| 1,831,457 A | 11/1931 | Larsen |
| 1,852,445 A | 4/1932 | Calkins et al. |
| 2,012,836 A | 8/1935 | Talbot et al. |
| 2,122,991 A | 7/1938 | Polston |
| 2,240,888 A | 5/1941 | Hageline |
| 2,426,808 A | 9/1947 | Auer |
| 2,642,256 A | 6/1953 | Stehlin |
| 2,712,881 A | 7/1955 | Mathisen |
| 2,736,201 A | 2/1956 | Ohlsen et al. |
| 2,767,587 A | 10/1956 | Perkins |
| 2,776,473 A | 1/1957 | Dailey et al. |
| 2,779,350 A | 1/1957 | Owens |
| 2,844,964 A | 7/1958 | Guibert |
| 2,859,932 A | 11/1958 | Mackal |
| 2,865,394 A | 12/1958 | Presley |
| 2,872,817 A | 2/1959 | Pitts |
| 2,952,269 A | 9/1960 | Stehlin |
| 2,994,224 A | 8/1961 | Brown |
| 3,038,485 A | 6/1962 | Hosek |
| 3,097,532 A | 7/1963 | Brown et al. |
| 3,219,047 A | 11/1965 | Kircher, III et al. |
| 3,223,100 A | 12/1965 | Koenig et al. |
| 3,244,376 A | 4/1966 | Thompson |
| 3,260,120 A | 7/1966 | Stilwell |
| 3,276,447 A | 10/1966 | Hamilton |
| 3,319,622 A | 5/1967 | Shiner |
| 3,390,677 A | 7/1968 | Razimbaud |
| 3,424,181 A | 1/1969 | Morse |
| 3,479,880 A | 11/1969 | Mutter et al. |
| 3,525,350 A | 8/1970 | Hosek |
| 3,621,719 A | 11/1971 | Goodman et al. |
| 3,633,621 A | 1/1972 | Myers |
| 3,638,499 A | 2/1972 | Saint-Andre |
| 3,678,959 A | 7/1972 | Liposky |
| 3,696,932 A | 10/1972 | Rosenberg |
| 3,736,099 A | 5/1973 | Begg et al. |
| 3,747,411 A | 7/1973 | McDermott et al. |
| 3,776,042 A | 12/1973 | Werra et al. |
| 3,779,082 A | 12/1973 | Galloway |
| 3,802,782 A | 4/1974 | Natelson |
| 3,848,581 A | 11/1974 | Cinqualbre et al. |
| 3,858,449 A | 1/1975 | Singer |
| 3,921,456 A | 11/1975 | Newcomb, Jr. et al. |
| 3,985,332 A | 10/1976 | Walker |
| 4,015,631 A | 4/1977 | Hayes |
| 4,018,059 A | 4/1977 | Hatch |
| 4,034,775 A | 7/1977 | Slagel |
| 4,055,179 A | 10/1977 | Manschot et al. |
| 4,061,709 A | 12/1977 | Miller et al. |
| 4,064,003 A | 12/1977 | Newton |
| 4,094,197 A | 6/1978 | Harris, Sr. et al. |
| 4,207,922 A | 6/1980 | Andrieux et al. |
| 4,244,224 A | 1/1981 | Conn |
| 4,294,247 A | 10/1981 | Carter et al. |
| 4,296,759 A | 10/1981 | Joslin et al. |
| 4,325,401 A | 4/1982 | Ukai et al. |
| 4,346,609 A | 8/1982 | Diesel |
| 4,353,386 A | 10/1982 | Slagel |
| 4,378,824 A | 4/1983 | Carder, Sr. |
| 4,423,641 A | 1/1984 | Ottung |
| 4,423,642 A | 1/1984 | Kuboichi |
| 4,454,772 A | 6/1984 | Brunner et al. |
| 4,458,543 A | 7/1984 | Mieth |
| 4,479,393 A | 10/1984 | Shores |
| 4,525,127 A | 6/1985 | Welker |
| 4,527,436 A | 7/1985 | Jones |
| 4,537,593 A | 8/1985 | Alchas |
| 4,557,151 A | 12/1985 | Welker |
| 4,569,236 A | 2/1986 | Kitchen et al. |
| 4,580,452 A | 4/1986 | Masson |
| 4,584,887 A | 4/1986 | Galen |
| 4,587,856 A | 5/1986 | Otis |
| 4,587,887 A | 5/1986 | Shibayama et al. |
| 4,622,457 A | 11/1986 | Bradley et al. |
| 4,630,847 A | 12/1986 | Blenkush |
| 4,657,027 A | 4/1987 | Paulsen |
| 4,669,312 A | 6/1987 | Maurer |
| 4,669,321 A | 6/1987 | Meyer |
| 4,704,910 A | 11/1987 | Conrad |
| 4,826,055 A | 5/1989 | Stull |
| 4,836,236 A | 6/1989 | Ladisch |
| 4,838,877 A | 6/1989 | Massau |
| 4,861,239 A | 8/1989 | Simmons et al. |
| 4,913,185 A | 4/1990 | Mattei |
| 4,941,517 A | 7/1990 | Galloway |
| 4,942,901 A | 7/1990 | Vescovini |
| 4,944,875 A | 7/1990 | Gaignet |
| 4,997,108 A | 3/1991 | Hata |
| 5,058,619 A | 10/1991 | Zheng |
| 5,095,765 A | 3/1992 | Filbey et al. |
| 5,117,872 A | 6/1992 | Yie |
| 5,158,558 A | 10/1992 | Melker et al. |
| 5,161,417 A | 11/1992 | Strong et al. |
| 5,177,872 A | 1/1993 | Lewis et al. |
| 5,246,204 A | 9/1993 | Ottung |
| 5,285,999 A | 2/1994 | Scholz |
| 5,296,197 A | 3/1994 | Newberg et al. |
| 5,360,413 A | 11/1994 | Leason et al. |
| 5,375,477 A | 12/1994 | Neill et al. |
| 5,398,557 A | 3/1995 | Shimizu et al. |
| 5,435,339 A | 7/1995 | Hayes |
| 5,452,746 A | 9/1995 | Hoobyar et al. |
| 5,463,908 A | 11/1995 | Rosolia et al. |
| 5,468,388 A | 11/1995 | Goddard et al. |
| 5,474,546 A | 12/1995 | Ambrisco et al. |
| D366,935 S | 2/1996 | Arthun et al. |
| 5,520,218 A | 5/1996 | Hlavinka et al. |
| 5,525,301 A | 6/1996 | Newberg et al. |
| 5,533,983 A | 7/1996 | Haining |
| 5,535,635 A | 7/1996 | Shaw |
| 5,542,305 A | 8/1996 | Hollinger |
| 5,549,568 A | 8/1996 | Shields |
| 5,585,576 A | 12/1996 | Jaeger |
| D381,067 S | 7/1997 | Karmalm |
| 5,730,418 A | 3/1998 | Feith et al. |
| 5,747,708 A | 5/1998 | Weiberth |
| 5,755,155 A | 5/1998 | Buesing |
| 5,766,462 A | 6/1998 | Jones |
| 5,786,209 A | 7/1998 | Newberg |
| 5,820,614 A | 10/1998 | Erskine et al. |
| 5,829,425 A | 11/1998 | Woods et al. |
| 5,868,433 A | 2/1999 | Matkovich |
| 5,885,255 A | 3/1999 | Jaeger, Jr. et al. |
| 5,897,526 A | 4/1999 | Vaillancourt |
| 5,911,252 A | 6/1999 | Cassel |
| 5,948,998 A | 9/1999 | Witte et al. |
| 6,009,684 A | 1/2000 | Buesing |
| 6,030,578 A | 2/2000 | McDonald |
| 6,032,543 A | 3/2000 | Arthun et al. |
| 6,068,617 A | 5/2000 | Richmond |
| 6,096,011 A | 8/2000 | Trombley, III et al. |
| 6,133,022 A | 10/2000 | Newberg |
| 6,145,810 A | 11/2000 | Connolly et al. |
| 6,156,025 A | 12/2000 | Niedospial, Jr. et al. |
| 6,162,206 A | 12/2000 | Bindokas et al. |
| 6,170,800 B1 | 1/2001 | Meloul et al. |
| 6,196,522 B1 | 3/2001 | Yuen et al. |
| 6,210,372 B1 | 4/2001 | Tessmann et al. |
| 6,221,041 B1 | 4/2001 | Russo |
| 6,237,639 B1 | 5/2001 | Jougla et al. |
| 6,254,773 B1 | 7/2001 | Biltoft |
| 6,273,869 B1 | 8/2001 | Vaillancourt |
| 6,306,191 B1 | 10/2001 | McInerney et al. |
| 6,314,987 B1 | 11/2001 | Hay |
| 6,345,640 B1 | 2/2002 | Newberg |
| 6,345,645 B1 | 2/2002 | Kenna et al. |
| D454,173 S | 3/2002 | Almasian et al. |
| 6,354,466 B1 | 3/2002 | Karpisek |
| 6,357,306 B1 | 3/2002 | Jaeger |
| 6,360,794 B1 | 3/2002 | Turner |
| 6,386,137 B1 | 5/2002 | Riche |
| 6,390,127 B2 | 5/2002 | Schick |
| 6,477,906 B1 | 11/2002 | Peterson |
| 6,516,677 B1 | 2/2003 | Suter |

| | | | | | | |
|---|---|---|---|---|---|---|
| 6,558,365 | B2 | 5/2003 | Zinger et al. | DE | 8812723 U1 | 12/1988 |
| 6,568,844 | B1 | 5/2003 | Arthun et al. | DE | 10039196 A1 | 12/2002 |
| 6,601,823 | B2 | 8/2003 | Newberg | DE | 69807924 T2 | 1/2003 |
| 6,623,631 | B1 | 9/2003 | Graus et al. | DE | 60310700 | 10/2007 |
| 6,648,006 | B1 | 11/2003 | Ostergaard | EP | 0103396 A2 | 3/1984 |
| 6,672,561 | B2 | 1/2004 | Kerg et al. | EP | 0107579 A2 | 5/1984 |
| 6,699,229 | B2 | 3/2004 | Zinger et al. | EP | 0154002 | 9/1985 |
| 6,715,624 | B2 | 4/2004 | Brockwell | EP | 0508749 A2 | 10/1992 |
| 6,779,575 | B1 | 8/2004 | Arthun | EP | 0510355 A1 | 10/1992 |
| 6,860,162 | B1 | 3/2005 | Jaeger | EP | 0576380 A1 | 12/1993 |
| 6,871,669 | B2 | 3/2005 | Meyer et al. | EP | 0468957 B1 | 6/1994 |
| 6,902,144 | B2 | 6/2005 | deCler | EP | 0684050 A2 | 11/1995 |
| 6,916,012 | B2 | 7/2005 | Newberg | EP | 0691492 A1 | 1/1996 |
| 7,137,974 | B2 | 11/2006 | Almasian et al. | EP | 1008359 A1 | 6/2000 |
| 7,195,181 | B2 * | 3/2007 | Steingass et al. ......... 239/581.1 | EP | 1231699 A1 | 8/2002 |
| 7,272,981 | B2 | 9/2007 | Bigalke | EP | 1321699 A2 | 6/2003 |
| 7,273,550 | B2 | 9/2007 | Gutman et al. | EP | 1329210 A1 | 7/2003 |
| 7,293,475 | B2 | 11/2007 | Furey et al. | EP | 1548420 A2 | 6/2005 |
| 7,293,477 | B2 | 11/2007 | Furey et al. | EP | 1370788 B1 | 11/2005 |
| 7,350,535 | B2 | 4/2008 | Liepold et al. | EP | 0858589 B1 | 12/2005 |
| 7,473,360 | B2 | 1/2009 | Hoffman et al. | EP | 1499382 B1 | 12/2006 |
| 7,488,446 | B2 | 2/2009 | Meyer et al. | EP | 1962076 A2 | 8/2008 |
| 7,578,205 | B2 | 8/2009 | Belongia | FR | 2023259 A1 | 8/1970 |
| 7,578,936 | B2 | 8/2009 | Gaignet et al. | GB | 943132 | 11/1963 |
| 7,597,683 | B2 | 10/2009 | Myhrberg et al. | GB | 1381391 | 1/1975 |
| RE41,169 | E | 3/2010 | Arthun | GB | 1418046 | 12/1975 |
| 7,722,733 | B2 | 5/2010 | Tomasetti et al. | GB | 1463303 | 2/1977 |
| 7,753,340 | B2 | 7/2010 | Liepold et al. | GB | 1479226 | 7/1977 |
| 7,815,362 | B2 | 10/2010 | Myhrberg et al. | GB | 1511240 | 5/1978 |
| 7,921,740 | B2 | 4/2011 | Furey et al. | GB | 1573482 | 8/1980 |
| 7,927,316 | B2 | 4/2011 | Proulx et al. | GB | 2327369 A | 1/1999 |
| 7,959,754 | B2 | 6/2011 | Arthun | GB | 2365511 A | 2/2002 |
| 8,029,023 | B2 | 10/2011 | Arthun et al. | JP | 42-15498 U | 9/1967 |
| 8,167,480 | B2 | 5/2012 | Myhrberg et al. | JP | 44-4942 U | 2/1969 |
| 8,281,961 | B2 | 10/2012 | Martin | JP | 49-112631 U | 9/1974 |
| 2002/0129858 | A1 | 9/2002 | Meyer et al. | JP | 58-131802 U | 9/1983 |
| 2003/0188588 | A1 | 10/2003 | Jaeger | JP | 59-38278 U | 3/1984 |
| 2005/0016620 | A1 | 1/2005 | Proulx et al. | JP | 02-052667 | 2/1990 |
| 2005/0035597 | A1 * | 2/2005 | Bamberger et al. ........... 285/340 | JP | 2-71728 A | 3/1990 |
| 2005/0090797 | A1 | 4/2005 | Almasian et al. | JP | 02-118276 | 5/1990 |
| 2005/0132821 | A1 | 6/2005 | Furey et al. | JP | 2-121679 U | 10/1990 |
| 2005/0150546 | A1 | 7/2005 | Liepold et al. | JP | 3-141948 A | 6/1991 |
| 2005/0285066 | A1 | 12/2005 | Huang | JP | 6-10845 U | 2/1994 |
| 2006/0081804 | A1 | 4/2006 | Cong | JP | 6-23045 A | 2/1994 |
| 2006/0086922 | A1 | 4/2006 | Jensen et al. | JP | 6-327772 | 11/1994 |
| 2006/0091060 | A1 | 5/2006 | Gutman et al. | JP | 7-051371 | 2/1995 |
| 2006/0142730 | A1 | 6/2006 | Proulx et al. | JP | 8-502339 A | 3/1996 |
| 2006/0201263 | A1 | 9/2006 | Furey et al. | JP | 8-168535 | 7/1996 |
| 2006/0211995 | A1 | 9/2006 | Myhrberg et al. | JP | 9-154945 | 6/1997 |
| 2006/0243942 | A1 | 11/2006 | Liepold et al. | JP | 9-154945 A | 6/1997 |
| 2006/0272432 | A1 | 12/2006 | Belongia | JP | 9-512892 A | 12/1997 |
| 2007/0106264 | A1 | 5/2007 | Proulx et al. | JP | 11-141713 | 5/1999 |
| 2007/0193375 | A1 | 8/2007 | Pandori et al. | JP | 11-270705 | 10/1999 |
| 2007/0253287 | A1 | 11/2007 | Myhrberg et al. | JP | 11-514741 | 12/1999 |
| 2008/0000820 | A1 | 1/2008 | Mitchell | JP | 2000-055792 | 2/2000 |
| 2008/0022785 | A1 | 1/2008 | Furey et al. | JP | 2001-170188 | 6/2001 |
| 2008/0087860 | A1 | 4/2008 | Vaillancourt et al. | JP | 2001-170188 A | 6/2001 |
| 2008/0103476 | A1 | 5/2008 | Schulte | JP | 2001-269401 | 10/2001 |
| 2008/0185552 | A1 | 8/2008 | Myhrberg et al. | JP | 2001-269401 A | 10/2001 |
| 2008/0277878 | A1 | 11/2008 | Arthun et al. | JP | 2001-523525 A | 11/2001 |
| 2009/0019952 | A1 | 1/2009 | Furey et al. | JP | 2002-510996 A | 4/2002 |
| 2009/0054758 | A1 | 2/2009 | Dunseath | JP | 2004-332797 A | 11/2004 |
| 2009/0101575 | A1 * | 4/2009 | Alburty et al. ................ 210/636 | JP | 2005-181336 A | 7/2005 |
| 2009/0229671 | A1 | 9/2009 | Hartnett et al. | JP | 2005-519825 | 7/2005 |
| 2009/0250157 | A1 | 10/2009 | Arthun | JP | 2006-516723 A | 7/2006 |
| 2010/0123094 | A1 | 5/2010 | Zumbrum | JP | 2008-185218 | 8/2008 |
| 2010/0133459 | A1 | 6/2010 | Zumbrum | JP | 2009-002965 | 1/2009 |
| 2010/0154569 | A1 | 6/2010 | Guedon | JP | 4332106 B2 | 6/2009 |
| 2010/0158759 | A1 | 6/2010 | Olivier | JP | 2009-192540 | 8/2009 |
| 2010/0290311 | A1 | 11/2010 | Myhrberg et al. | SU | 649954 A | 2/1979 |
| 2010/0326212 | A1 | 12/2010 | Furey et al. | WO | 86/02450 A1 | 4/1986 |
| 2011/0155258 | A1 | 6/2011 | Zumbrum | WO | 90/12972 A1 | 11/1990 |
| 2011/0155274 | A1 | 6/2011 | Zumbrum | WO | 91/00215 A1 | 1/1991 |
| 2011/0197989 | A1 | 8/2011 | Proulx et al. | WO | 94/08173 A1 | 4/1994 |
| | | | | WO | 94/19086 A1 | 9/1994 |
| | | FOREIGN PATENT DOCUMENTS | | WO | 95/30856 A1 | 11/1995 |
| DE | | 3215799 A | 11/1983 | WO | 96/30076 A1 | 10/1996 |
| DE | | 3633431 A1 | 4/1988 | WO | 97/16715 A1 | 5/1997 |
| DE | | 3701250 A1 | 7/1988 | WO | 98/45188 A1 | 10/1998 |

| | | | |
|---|---|---|---|
| WO | 98/50105 A1 | 11/1998 |
| WO | 99/03568 A1 | 1/1999 |
| WO | 99/06089 A1 | 2/1999 |
| WO | 99/26580 A1 | 6/1999 |
| WO | 00/78472 A1 | 12/2000 |
| WO | 03/090842 A1 | 11/2003 |
| WO | 03/090843 A1 | 11/2003 |
| WO | 2005/012775 A1 | 2/2005 |
| WO | 2006/022816 A2 | 3/2006 |
| WO | 2006/026253 A2 | 3/2006 |
| WO | 2008/042285 A2 | 4/2008 |
| WO | 2008/048511 A2 | 4/2008 |
| WO | 2008/136720 A1 | 11/2008 |
| WO | 2010/008395 A1 | 1/2010 |
| WO | 2010/008396 A2 | 1/2010 |
| WO | 2013/011231 A1 | 1/2013 |

OTHER PUBLICATIONS

Process Worldwide-PharnnaTEC Jun. 2004, dated Jun. 2004, "Bridging the gap; A case study in the validation of hybrid connectors", 3-pages.

Gore's First Supplemental Response to Millipore's First Set of Interrogatories [Interrogatory Nos. 11, 15 and 16], Civil Action No. 11-346-SLR, United States District Court for the District of Delaware, dated Nov. 1, 2011, 86-Pages.

File history of U.S. Appl. No. 78/140,217, filed Jul. 1, 2002, 53-Pages.

Office Action dated Apr. 6, 2010 in co-pending U.S. Appl. No. 11/878,126.

Millipore Publication, NovAseptic, NovaSeptum Liquid Sampling System, dated Nov. 2001, P75185, Rev. B (Bates stamp—WLG-DEL00040809-WLG-DEL00040813), 6 pages.

ITT Fluid Technology Corp, "Pure-Flo: Sample and Bleed Valves for the pharmaceutical and bioprocessing industries", BSV-92, dated Sep. 1992 (Bates stamp WLG=DEL00039389—WLG-DEL00039394), 6-Pages.

Sani-Tech Globe & Angle Valve product information, dated Aug. 1989 (Bates stamp WLG-DEL00040302—WLG-DEL00040304), 3 pages.

Waukesha Cherry-Burrell Manual Valves, dated May 2000 (Bates stamp CSMI000044-CSMI000066), 23-pages.

Millipore Publication, ESP Sanitary Sample Valves, Operation and Maintenance Instructions, dated Nov. 1995, P17262, Rev. B, (WLG-DEL00039664—WLG-DEL00039678), 16-pages.

Correspondence from T. Pender to C. Burrell dated Dec. 2, 2011 regarding C.A. No. 11-CV-346-SLR (Bates Stamp GF000001-GF000008), 8 pages.

Documents Produced by Third Party Casella Sales and Marketing Inc., related to *W. L. Gore* v. *Millipore Subpoena*, Nov. 2011, Bates No. CSMI000001 through CSMI000066, 65 pages.

Office Action mailed Aug. 25, 2011 in co-pending U.S. Appl. No. 11/350,384.

Final Rejection mailed Mar. 5, 2012 in co-pending U.S. Appl. No. 11/350,384.

Notice of Allowance mailed Mar. 29, 2012 in co-pending U.S. Appl. No. 12/284,666.

European communication dated Oct. 29, 2010 in a co-pending foreign application (EP10179151.5).

European communication dated Oct. 29, 2010 in a co-pending foreign application (EP10179183.8).

Indian communication dated Oct. 18, 2010 in a co-pending foreign application (IN1444/DELNP/2004).

International Search Report for PCT/US03/12927 dated Aug. 6, 2003.

International Preliminary Examination Report for PCT/US03/12937 dated Feb. 11, 2004.

International Search Report for PCT/US03/13073 dated Aug. 6, 2003.

European Search Report dated Mar. 13, 2006 (EP1548420).

International Search Report for PCT/US03/12924 dated Aug. 6, 2003.

International Preliminary Examination Report for PCT/US03/12924 dated Jul. 8, 2004.

Gore's Preliminary Invalidity Contentions to Plaintiff Millipore Corporation, Document No. 21, filed Oct. 29, 2009 in the United States District Court for the District of Massachusetts, Civil Action No. 09-10765 DPN.

Pharmaceutical Processing, p. 8 (Jan. 1, 2001); Janetschek, Robert; "Capsule Filters & Disposable Sterile Processing Systems".

Pharmaceutical Processing, p. 8 (Jan. 1, 2002); Charter Medical Ltd, Bioprocess Products, "New Quality of data for Bioprocessing bags".

Chemical Engineering Progress, pp. 10-11 (Nov. 2002); Green, Richard et al.; "Disposable Equipment: A Mainstay in Bioprocessing".

Biopharm International, p. 18, Jul. 1, 2003; Wendt, Denise; "BioTrends: Disposable Processing Systems; How Suppliers Are Meeting Today's Biotech Challenges from Fluid Handling to Filtration".

CleanRooms, 5-pages; Jun. 2004, Haughney, Holly et al.; "Taking Disposable Processing to the Next Level".

Alternative Manufacturing, CleanRooms p. S4-S9 (Feb. 2003); Tingley, Steve; "Plastic Factory: Disposable Biopharmaceutical Manufacturing Takes a Giant Leap Forward".

Alternative Manufacturing, CleanRooms p. 12-14 (Jun. 2003); Tingley, Steve; "Plastic Factory II: The Final Pieces of the Disposable Puzzle".

BioPharm International, p. 50, Oct. 1, 2003, Aranha, Hazel et al.; "Disposable Processing Gains You a Competitive Edge: Enhancing Manufacturing Capacity with Disposable Filters, Connectors, and Membrane Chromatography".

Millipore's Initial Infringement Contentions, Document 19, filed Oct. 8, 2009 in the United States District Court for the District of Massachusetts, Civil Action No. 09-10765 DPW.

Gore's Preliminary Non-Infringement Contentions to Plaintiff Millipore Corporation, Document 20, filed Oct. 29, 2009 in the Untied States District Court for the District of Massachusetts, Civil Action No. 09-10765 DPW.

Lynx ST Connectors http://www.millipore.com/catalogue/module/c9131 dated Oct. 30, 2009.

Pure-Flo Hygienic diaphragm valves, actuators, and switch packages, http://www.ittpureflo.com/valvetype.html dated Oct. 30, 2009.

About Fluid Line Technology, http://www/fluidlinetech.com/aboutus.html dated Oct. 30, 2009.

Valves, Gemu Valves and Distributor, Diaphragm Valves, Sanitary Valves, Aseptic Valves, Valves and Fittings, http://www.casellasales.com, dated Oct. 30, 2009.

Allegro Singe-Use Systems—Recommended Capsule Filters and Membranes, http://www.pall.com/variants/print/biopharm_48022.asp dated Oct. 30, 2009.

Colder Products—Quick Couplings & Fittings for Industrial Applications—Industrial Products, http://www.colder.com/Markets/Industrial/IndustrialProducts/tabid/821/Default.aspx?ProductId=22, dated Oct. 30, 2009.

NovAseptic—How to Use NA sampling system, http://www.novaseptic.se/main.as?typ+6 dated Feb. 13, 2002.

Steam-In-Place Bag Connector, http://www.fluidcomponents.net/tc_tech.html, download on Feb. 18, 2010.

Pharmenta AptiPort Sampling Valve, http//www.web.archive.org/web/20031029084907/http://www.pharmenta.com/aptiport.htm, dated Feb. 18, 2010.

Process PharmaTEC Interantional, issue Jun. 2004 (RP1007EN00), pp. 16-17 (Nov. 2004); Landon, R. et al.; "Bridging the Gap".

Daily Business Briefing—"Entegris Inroduces the First All Teflon PFA" dated Apr. 16, 2002.

Lea & Febiger (Fourth Edition); "Disinfection, Sterilization, and Preservation", Block, Seymour S., ISBN:0-8121-1364-0 (1991).

Japanese communication dated Jul. 27, 2010 in co-pending foreign application (JP2008-070904).

Japanese communication dated Dec. 1, 2010 in co-pending foreign application.

Memorandum and Order, Document No. 70, dated Sep. 20, 2010, in the United States District Court for the District of Massachusetts, Civil Action No. 09-10765-DPW.

Opticap Valve; Millipore Application Note, Jul. 2000, "Gamma Compatible Sterilizing Grade Filter Capsules for Use with Disposable Manufacturing Container"; 6-Pages.

Opticap Vent; Millipore Data Sheet, Apr. 2005, "Gamma Compatible Sterilizing-grade Durapore 0.1 um and 0.22 um Filters"; 8-pages.
Opticap3; Millipore, Nov. 2001, "OpticapTM Capsules with Millistake+TM Media User Guide", 4-Pages.
NovaSeptum, NovAseptic, Feb. 2003, "NovaSeptum Liquid Sampling System", 4-Pages.
Microbiological Analysis, Sampling Ports, 1989, p. 130.
Lynx Trademark (Reg. No. 2,831,931; Apr. 1, 2003).
Office Actions dated Sep. 22, 2005, Apr. 21, 2006, Nov. 16, 2006, Sep. 10, 2007, Apr. 15, 2008, Nov. 28, 2008, Apr. 14, 2009, Jan. 25, 2010, Apr. 15, 2010, Aug. 12, 2010 and Dec. 7, 2010 in co-pending U.S. Appl. No. 10/500,077.
Office Actions dated Sep. 19, 2009 and May 12, 2010 in co-pending U.S. Appl. No. 11/350,384.
Office Actions dated Mar. 16, 2010 and Oct. 7, 2010 in co-pending U.S. Appl. No. 11/584,301.
Office Actions dated Jan. 30, 2009, Jun. 26, 2009, Aug. 12, 2009, Sep. 25, 2009, Apr. 6, 2010 and Feb. 16, 2011 in co-pending US application.
Office Actions dated Mar. 19, 2010, Oct. 1, 2010, Oct. 7, 2010, Oct. 15, 2010 and Oct. 20, 2010 in co-pending US application.
European Communication mailed Feb. 2, 2010 in co-pending European Patent Application No. 09290917.5 5 pages.
European Communication mailed Jan. 29, 2010 in co-pending European Patent Application No. 09290918.3 6 pages.
Gore's Fourth Supplemental Response to Millipore's First Set of Interrogatories [Interrogatories Nos. 11 and 12], Civil Action No. 11-346-SLR in the USDC for the District of Delaware, dated May 9, 2012, 172 pages.
New quality of data for bioprocessing bags. (Application Area). Pharmaceutical Processing, Jan. 2002, Charter Medical, Ltd., Bioprocess Products, Retrieved from the Internet: <URL: http://www.accessmylibrary.com/coms2/summary_0286-25022745_ITM>, pp. 1-2.
Risk Free Connection of Sterilized Single-Use Fluid Path Assemblies to Stainless Steel SIP Systems with Lynx ST (Steam-To) Connectors [online], Millipore Corporation Application Note, 2008. Retrieved from the Internet: www.millipore.com (8 pages).
Office Action mailed Jun. 26, 2012 in co-pending U.S. Appl. No. 12/872,436.
English translation of Chinese Communication issued Aug. 29, 2012 in corresponding Chinese patent application No. CN 201010531386.0.
Japanese Communication, with English translation, dispateched Aug. 21, 2012 in corresponding Japanese patent application No. JP 2010-245357.
Office Action mailed Oct. 3, 2012 in co-pending U.S. Appl. No. 13/092,566.
Office Action mailed Oct. 5, 2012 in co-pending U.S. Appl. No. 12/291,814.
Final Rejection mailed Oct. 10, 2012 in co-pending U.S. Appl. No. 12/872,436.
Office Action mailed Nov. 30, 2012 in co-pending U.S. Appl. No. 12/284,666.
Office Action mailed Dec. 21, 2012 in co-pending U.S. Appl. No. 12/638,283.
Entegris Impact Asymmetric Disposable Filters, Product Information brochure, 4414-5723ENT-0511, 2006, 6 pages.
Entegris Impact Mini Disposable Filters, Product Information brochure, 4414-2646ENT-1006, 2006, 4 pages.
Millipore Corporation, Milli-Q Direct Water Purification System brochure, Lit. No. PB1032EN00, Jan. 2012, 8 pages.
Millipore Corporation, Milli-Q Advantage A10 Water Purification Systems brochure, Lit. No. PB0001EN00, 2013, 12 pages.
International Search Report on PCT/US2008/070482, date of mailing: Apr. 16, 2009, 2 pages.
Written Opinion of the International Searching Authority (Appln. No. PCT/US2008/070482, filed Jul. 18, 2008) mailed Apr. 16, 2009, 4 pages.
International Search Report on PCT/US2011/021341, date of mailing: Sep. 27, 2011, 4 pages.
International Preliminary Report on Patentability (Appln. No. PCT/US2008/070482, filed Jul. 18, 2008) mailed Jan. 27, 2011, pp. 1-6.
International Preliminary Report on Patentability (Appln. No. PCT/US2008/070488, filed Jul. 18, 2008) mailed Jan. 27, 2011, pp. 1-6.
Japanese Communication mailed Dec. 6, 2011 in co-pending Japanese Patent Application No. 2009-282419, 6 pages.
French Search Report mailed Nov. 13, 2009 in co-pending French Patent Application No. FR 0858804.
French Search Report mailed Nov. 20, 2009 in co-pending French Patent Application No. FR 0858805.
Extended European Search Report mailed Dec. 21, 2010 in co-pending European Patent Application No. 08253748.1.
Preliminary Noninfringement and Invalidity Disclosures of Allpure Technologies, Inc., Document 22, filed Jul. 20, 2011 in the United States District Court for the District of Massachusetts, Civil Action No. 11-cv-10221-DPW, 15 pages.
Allegheny Bradford Corporation's Objections and Responses to Subpoena, Civil Action No. 1:11-cv-00346-SLR, dated Dec. 15, 2011 in the USDC for the District of Delaware, and Bates # ABC00001 through Bates # ABC000012, 19 pages.
Fluid Line Technology Corporation Documents produced in Gore v. Millipore, Nov. 28, 2011, Bates # FLT000001 through Bates # FLT000103, 48 pages.
File history of U.S. Appl. No. 60/375,747 (application filed Apr. 26, 2002), Document 53-2, Case 1:09-cv-10765-DPW, filed May 25, 2010, 50 pages.
File history of U.S. Appl. No. 60/500,024 (application filed Sep. 4, 2003), 23 pages.
Casella Sales & Marketing Inc., CSMI Sample Valves. Datasheet [online]. Retrieved from the Internet: www.casellasales.com (2 pages), 2007.
Fluid Line Technology Corporation, FLT Bleed/Sample Valve Maintenance, Nov. 10, 2008. Datasheet [online], Fluid Line Technology. Retrieved from the Internet: www.fluidlinetech.com (1 page).
Sanitary Inline Bleed and Sample Valves. Datasheet [online], Fluid Line Technology, Retrieved from the Internet: www.fluidlinetech.com (1 page).
ITT Dualrange Control Valve. Data Sheet [online], Pure-Flo. Retrieved from the Internet: www. ittpureflo.com (2 pages).
ITT Sample & Bleed Valves. Datasheet [online], ITT Corporation, 2006. Retrieved from the Internet: www.ittpureflo.com (4 pages).
Guidelines for Using the Lynx ST Connector. Technical Brief [online], Millipore Corporation, 2008. Retrieved from the Internet: www/millipore.com (2 pages).
"Connecting the Sanitary Flange," Datasheet [online], Millipore Corporation, 2007 (pp. 1-2).
Pure-Flo Solutions, Pure-Flo Radial Seated Tank Bottom Diaphragm Valve, Datasheet [online], ITT Industries, 2001. (2 pages).
"Sip-Able Sample Valve," Datasheet [online]. Retrieved from the Internet: www.fluidlinetech.com (1 page).
"Rapid Aseptic Fluid Transfer System Introduction" Stedim Blosystems. [online]. Retrieved from the Internet: <URL: http: www.stedim.com/p2A_IDC_introduction.php> (2 pages), dated Nov. 21, 2007.
Notice of Allowance dated Mar. 1, 2011 in co-pending U.S. Appl. No. 11/878,126.
Miscellaneous Communication mailed Apr. 18, 2012 and Apr. 16, 2012 in co-pending U.S. Appl. No. 12/284,666.
Office Action mailed Dec. 8, 2011 in co-pending U.S. Appl. No. 12/291,814.
Final Rejection mailed Jun. 20, 2012 in co-pending U.S. Appl. No. 12/291,814.
Office Action mailed Sep. 30, 2011 in co-pending U.S. Appl. No. 12/638,242.
Notice of Allowance Feb. 16, 2012 in co-pending U.S. Appl. No. 12/638,242.
Japanese Communication, with English translation, mailed Feb. 5, 2013 in co-pending Japanese Patent Application No. JP 2011-179614.
Japanese Communication, with English translation, mailed Mar. 26, 2013 in co-pending Japanese Patent Application No. 2008-288424.
Notice of Allowance mailed Mar. 22, 2013 in co-pending U.S Appl. No. 13/092,566.
Notice of Allowance mailed Apr. 22, 2013 in co-pending U.S. Appl. No. 11/584,301.

Office Action mailed May 03, 2013 in co-pending U.S. Appl. No. 12/872,436.
Notice of Allowance mailed Jun. 3, 2013 in co-pending U.S. Appl. No. 12/638,283.
Memorandum and Order Denying Millipore's Motion to Alter Judgment and for Reconsideration, U S District Court for The District of Massachusetts, *EMD Millipore Corporation v. W. L. Gore & Associates, Inc.*, Civil Action No. 09-10765-DPW, Document 83, Dated Mar. 20, 2012, 16 pages.
Gore's Prior Art Statement with Exhibits A through I (entire document), U S District Court for the District of Delaware, *W. L Gore & Associates, Inc. v. EMD Millipore Corporation*, Civil Action No. 11-346-SLR, Dated Dec. 21, 2011, 55 pages.
Millipore's List of Claim Terms to Be Construed and Proposed Constructions, U S District Court for the District of Delaware, *W. L. Gore & Associates, Inc. v. EMD Millipore Corporation*, Civil Action No. 11-346-SLR, Dated May 30, 2012, 8 pages.
Gore's List of Claim Terms and Proposed Constructions, U S District Court for the District of Delaware, *W. L. Gore & Associates, Inc. v. EMD Millipore Corporation*, Civil Action No. 11-346-SLR, Dated May 30, 2012, 4 pages.
Millipore's Responsive Constructions of Claim Terms, U S District Court for the District of Delaware, *W. L. Gore & Associates, Inc. v. EMD Millipore Corporation*, Civil Action No. 11-346-SLR, Dated Jun. 20, 2012, 5 pages.
Gore's List of Responsive Claim Constructions, U S District Court for the District of Delaware, *W. L. Gore & Associates, Inc. v. EMD Millipore Corporation*, Civil Action No. 11-346-SLR, Dated Jun. 27, 2012, 8 pages.
Gore's Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 71, Dated Aug. 8, 2012, 3 pages.
Exhibits 1 and 2 to Gore's Motion for Leave to Amend Its Complaint for Declaratory Judgment, US District Court for The District of Delaware, *W. L. Gore & Associates, Inc. v. EMD Millipore Corporation*, Civil Action No. 11-346-SLR- MPT, Document 75, Redacted-Public Version, Dated Aug. 15, 2012, 241 pages.
Plaintiff Gore's Brief in Support of Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 76, Dated Aug. 15, 2012, Redacte—Public Version, 23 pages.
Aesseal Environmental Technology P04U and PO5U Single Bellows Component Seal Range, Jan. 2006, (Exhibit 4 to the Affidavit of Alexander H. Slocum, Ph.D., US District Court for the District of Massachusetts, *EMD Millipore Corporation v. AllPure Technologies, Inc.*, Civil Action No. 1:11-cv-10221-DPW,Document 66-4, dated May 2, 2012), 5 pages.
Purdue University-School of Mechanical Engineering-International Compressor Engineering Conference, article by J. W. Abar, "End Face Seals for Air-Conditioning Compressors", 1972 (Exhibit 5 to the Affidavit of Alexander H. Solcum, PhD, US District Court for the District of Massachusetts, *EMD Millipore Corporation v. AllPure Technologies, Inc.*, Civil Action No. 1:11-cv-10221-DPW, Document 66-5, dated May 2, 2012), 15 pages.
Memorandum and Order regarding Claim Construction, U S District Court for the District of Massachusetts, *EMD Millipore Corporation v. Allpure Technologies, Inc.*, Civil Action No. 11-10221-DPW, Document 81, Dated Oct. 11, 2012, 34 pages.
Photographs (7 photos) of the Millipore commercially needleless sampling device; available at least as of Feb. 14, 2012, 7 pages.
Photographs (3 photos) of the Millipore Opticap XLT base, commercially available in 2002, no earlier than Jan. 1, 2002, 3 pages.
Photographs (3 photos) of the Millipore Opticap XL 300, commercially available in 2002, no earlier than Jan. 1, 2002, 3 pages.

Brief for Plaintiff-Appellant, US Court of Appeals, Appeal Nos. 2011-1029, 2012-1371, *EMD Millipore Corporation v. W. L. Gore & Associates, Inc.*, Document 40, dated Jul. 25, 2012 and filed Jul. 27, 2012 , 147 pp., submitted in 2 parts.
Brief of Defendant-Appellee W. L. Gore & Associates, Inc., US Court of Appeals, Appeal Nos. 2011-1029, 2012-1371, *EMD Millipore Corporation v. W. L. Gore & Associates*, Inc., Document 52, filed Oct. 9, 2012, 75 pages.
Reply Brief for Plaintiff-Appellant, US Court of Appeals, Appeal Nos. 2011-1029, 2012-1371, *EMD Millipore Corporation v. W. L. Gore & Associates, Inc.*, Document 57, Dated Nov. 9, 2012, 42 pages.
AllPure Takeone Aseptic Sampling System Overview, 2 pgs. (Deposition Exhibit dated Nov. 12, 2012).
Amesil HF Silicone Steam Valve Aseptic Connector-Flow Control, 2 pages, Bates No. WLG00005888-WLG00005889 (WLG-DEL 00005946—WLG-DEL 00005947).
ASI Life Sciences, three 60, Single Use Aseptic Sampling System, www.asisus.com, Jan. 10, 2013, 8 pages.
Fluid Line Technology Corporation, Product Catalog, 32 pages, Bates No. FLT000003-FLT000034, on information and belief available as of about Nov. 2009.
Gore Single-Use Valve, for Steam-In-Place Applications, 4 pgs. 2009.
Gore STA-PURE Fluid Sampling System, for Single-Use Aseptic Applications, Secure Sampling for Bioprocessing Fluids, Dec. 2008, 4 pages.
Lynx ST Connectors, Millipore Data Sheet, Lit. No. 051750EN00, Rev. E, May 2008, 4 pages.
International Application No. PCT/US03/13073, filed Apr. 25, 2003, and Request for Express Abandonment of U.S. Appl. No. 10/423,131, filed Sep. 11, 2003, 56 pages.
MicropreSure Sanitary Sampling Valves, Millipore Data Sheet, Lit. No. DS1006EN00, May 2005, 4 pages.
Millipore Express SHF Hydrophilic Cartridge Filters, Data Sheet, May 16, 2013, www.millipore.com/catalogue, 2 pages.
Millipore, Hydrophilic Durapore Cartridges and Capsules User Guide, Lit. No. RF 1510EN00, Jan. 2002, 56 pages.
Millipore, Milliflex-P. Sanitary Sampling Valves, Operation and Maintenance Instructions, Jul. 2006, 17 pages.
NovaSeptum sampling systems, EMD Millipore Data Sheet, Jun. 2012, Lit. # DS0050EN00, Rev. E., 10 pgs.
NovaSeptum sampling systems, Merck Millipore Data Sheet, Apr. 2013, Lit. # DS0050EN00, Rev. H., 10 pgs.
Millipore, NovaSeptum AV Sterile Sampling System, for liquid sampling, User Guide, Lit. No. 00000069TP, Rev. A., Jun. 2006, 2 pages.
Millipore Opticap XL and XLT Disposable Capsules, Millipore Corporation, Lit. No. PB1700EN00, Rev. B, Jun. 2004, 4 pages.
Pharmaceutical Engineering, vol. 23, No. 3, May/Jun. 2002, pp. 1-8, "Single-Use Disposable Filling for Sterile Pharmaceuticals", Belongia, et al.
Redacted email, dated Jun. 4, 2012, regarding Disposable Steam Connector, 2 pages.
Millipore, Series 2000, Single Sanitary Cartridge Housing, Instructions for Installation and Maintenance, Lit. No. P35265, Rev. A, Feb., 2000, 12 pages.
ThermoScientific, Data Sheet 053, Rev. 2, "Aseptic Connection Devices", 2008, 2 pages.
Final Rejection mailed Jun. 19, 2013 in co-pending U.S. Appl. No. 12/291,814.
Notice of Allowance mailed Jun. 21, 2013 in co-pending U.S. Appl. No. 12/284,666.
Notice of Allowance mailed Jun. 8, 2013 in co-pending U.S. Appl. No. 12/284,666.
Notice of Allowance mailed Jul. 3, 2013 in co-pending U.S. Appl. No. 13/092,566.
Notice of Allowance mailed Jul. 5, 2013 in co-pending U.S. Appl. No. 11/584,301.

* cited by examiner

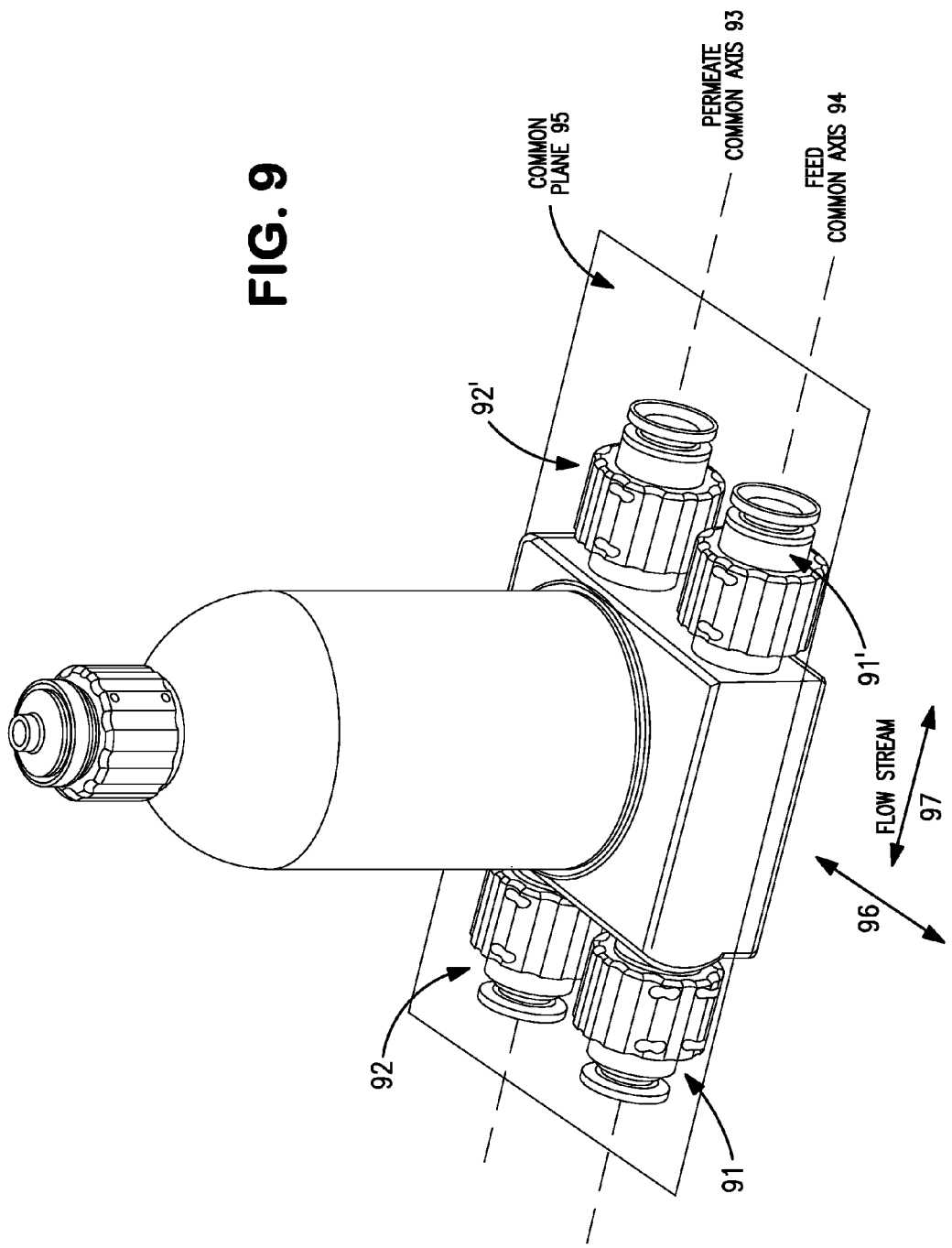

FLUID TRANSFER DEVICE AND SYSTEM

This application claims priority of U.S. Provisional Application Ser. No. 61/280,172 filed Oct. 30, 2009, the disclosure of which is incorporated herein by reference.

FIELD

The present disclosure relates to a fluid transfer device, and a system embodying the fluid transfer device. In certain embodiments, it relates to a disposable sterile fluid transfer device in the form of a valve particularly suited for use in the pharmaceutical and biopharmaceutical industries.

BACKGROUND

In the pharmaceutical, biotechnology and even food, beverage and cosmetics industries, it is often desired to provide a processing system that is capable of handling fluids in a sterile manner. This is designed to prevent unwanted, often dangerous organisms, such as bacteria as well as environmental contaminants, such as dust, dirt and the like from entering into the process stream and/or end product. It would be desirable to have a completely sealed system but this is not always possible with the processes that take place in production.

There is a need for the introduction or removal of materials from the process stream in order to add components of the product, such as media or buffers to a bioreactor; withdraw samples from the process stream to check for microbial contamination, quality control, process control, etc.; and to fill the product into its final container such as vials, syringes, sealed boxes, bottles and the like.

Typically, the systems have been made of stainless steel and the system is exposed to live steam before use and then cleaned with chemicals such as caustic solutions after use to ensure that all contaminants are removed.

Steaming is the most effective means of sterilization. The use of steam in a set system is known as steaming in place or SIP. Saturated steam carries 200 times the BTU heat transfer capacity of heated air because of the latent heat released by the steam as it changes from vapor to liquid. However, several disadvantages exist with the use of steam. Any connections to or openings of the system made after the system has been steamed in place must be aseptic so as not to contaminate the system. Although this can be done using aseptic connectors this procedure increases the risk of contamination of the entire system. One typically uses alcohol wipes or an open flame to clean the components to be connected, (e.g. connecting a sample collection bag to a system after SIP has occurred) and thus minimize the risk of contamination.

Also, the high temperatures and pressure differentials of the steam make the selection of filter materials and components very difficult and limited and even then an accidental pressure differential at high temperatures can cause a filter, membrane or other non-steel component to fail.

Additionally, such systems that are reused need to undergo rigorous testing and validation to prove to the necessary authorities that the system is sterile before each use. The expense of validation as well as the cleaning regiment required is very high and very time consuming (typically taking 1 to 2 years for approval). In addition, some components are very difficult to adequately clean after use in preparation for their next use. Manufacturers are looking for ways to reduce both their costs and the time to market for their products. One possible approach is to adopt an all disposable system that is set up in a sterile fashion, used and then thrown away.

Biopharmaceutical manufacturers continue to prefer fully disposable filtration solutions due to reduced cleaning and capital equipment costs. Users will either purchase individual components and assemble them into the desired fluid flow path, or purchase preassembled flow paths, such as Millipore's Mobius® Solutions. Commonly these components or assemblies are pre-sterilized by the vendor using gamma irradiation. This reduces the bioburden and allows the user to achieve higher levels of aseptic assurance.

Although it is impossible to insure completely sterile assemblies, there are methods to reduce the risk of environmental contamination. Pre-sterilized assemblies are commonly sold with aseptic connectors, such as Millipore's Lynx® S2S, where the connections can be made in a validated sterile way. These kinds of connectors help control contamination from environment. Some customers order filter assemblies with connectors that can be directly sterilized by the customer, such as Millipore's Lynx® ST. This kind of connector acts as a valve and isolates the pre-sterilized filtration area from the environment. The methods of connection and the ability to insure sterility are of great importance and can be improved.

Disposable filter capsules are commonly sold pre-sterilized and packaged in the common aseptic double bag so the customer can manage bioburden by removing one bag at a time at various steps along the assembly process. However, such capsules cannot be used with non-disposable equipment because there is no simple means to sterilize both the reused and disposable components after they are assembled together. Although the filter membranes can survive steam-in-place (SIP) the capsule housing softens and may rupture during the high pressure and temperature exposure. Some manufacturers use high performance materials to withstand the extreme conditions, which incur additional product cost. Even with the use of high performance materials, the capsule must be aseptically installed.

In addition, in the use of a capsule filter such as by pharmaceutical manufacturers, it may become necessary to isolate a single filter form other filters, in order to retain sterility during installation, or to sterilize fluid pathways up to the capsule, for example. Also, a plurality of capsule filters is often used in parallel or in series, thereby necessitating their interconnection. An integral capsule connector that provides a parallel connection capability is advantageous in that it avoids external piping.

It therefore would be desirable to provide a pre-sterilized capsule that can be attached to existing reusable processing equipment, or to disposable equipment, and which can be sterilized such as by steaming-in-place while reducing environmental exposure. It also would be desirable to provide a filtration unit having an integral pre-sterilized capsule attached, as well as to provide a manifold assembly including one or more pre-sterilized capsules.

SUMMARY

The fluid transfer apparatus disclosed herein relates to a sterile transfer device for fluids (e.g., liquids or gases). In certain embodiments, the apparatus comprises a body having a bore formed through at least a portion of its interior. Preferably, it is a central axial bore formed through the entire length of the body. Contained within the bore is a movable plunger. In certain embodiments, the plunger moves without changing the axial dimensions of the body; it does not telescope. A first end of the body contains a face designed to be attached to an upstream component. A second end of the body is connected to a downstream component such as a filter, pipeline, sample bag or the like. The plunger has corresponding first and second ends. The first end of the plunger, when it is in the closed position, is in alignment with the face of the body, which combined form a steamable surface and a sterile barrier against the environment to the remainder of the interior of the body, the plunger and downstream components. An outer annular collar is rotatable relative to the body and causes the plunger to move axially within the bore from an open position to a closed position.

In certain embodiments, the downstream components are assembled to the device and it is placed in the closed position. The entire device and downstream components can be sterilized, such as with gamma radiation. In use the device and downstream components are attached by the face to the upstream component such as a filter outlet, a tank outlet, or a "T" of a pipe, and secured in place. The system and the face of the device are then steam sterilized in place. The device is then selectively opened when needed, establishing a sterile fluid pathway through the device to the downstream components.

The fluid transfer apparatus thus provides a connector that can be used in either the traditional steel system or disposable system which provides both a means for steam sterilizing the mating point of the connector to the system as well as providing a sterile downstream area or component, in pre-sterile condition, that can be disposed of after use and not be re-cleaned. The non-telescoping articulation means that actuation of the device does not result in a change in connector length, thereby enabling a user to install a capsule filter between fixed position piping. The shut-off feature and design of the face seal isolates the capsule filter from steam that can be used to sterilize the upstream or downstream components or plumbing.

In certain embodiments, the connector or valve includes a body having a bore, a plunger axially moveable within the bore between a valve open position and a valve close position, and a cam actuator operatively connected to the plunger such that rotation of the cam actuator causes axial movement of the plunger in the bore from the valve open to the valve closed position. In certain embodiments, the valve includes a pair of radially inwardly extending plunger engaging members and a pair of radially outwardly extending cam actuator engaging members, the members providing the connection between the cam actuator and the plunger. In certain embodiments, the cam actuator includes first and second collars, each having a groove for receiving a respective one of the radially outwardly extending cam actuator engaging members in sliding relation.

The fluid transfer devices enabling efficient manifolding, where multiple filters can be configured in series or in parallel. This enables, for example, the use of different grade filters in series, redundant single grade filters in series, larger total filter area in parallel, connection to disposable capsule housings, and a compacted assembly to reduce the footprint. Multiple capsule feed inlets can be interconnected and share a common feed port without the need for external manifold piping. Integrity testing of the assemblies also can be easily carried out. For example, a capsule filter can be individually integrity tested without removing it from a manifold arrangement by properly configuring the various fluid transfer devices.

BRIEF DESCRIPTION OF THE DRAWINGS

FIG. 9 is a perspective view of a filter capsule with multiple fluid transfer devices in accordance with certain embodiments.

DETAILED DESCRIPTION

Figure 1:
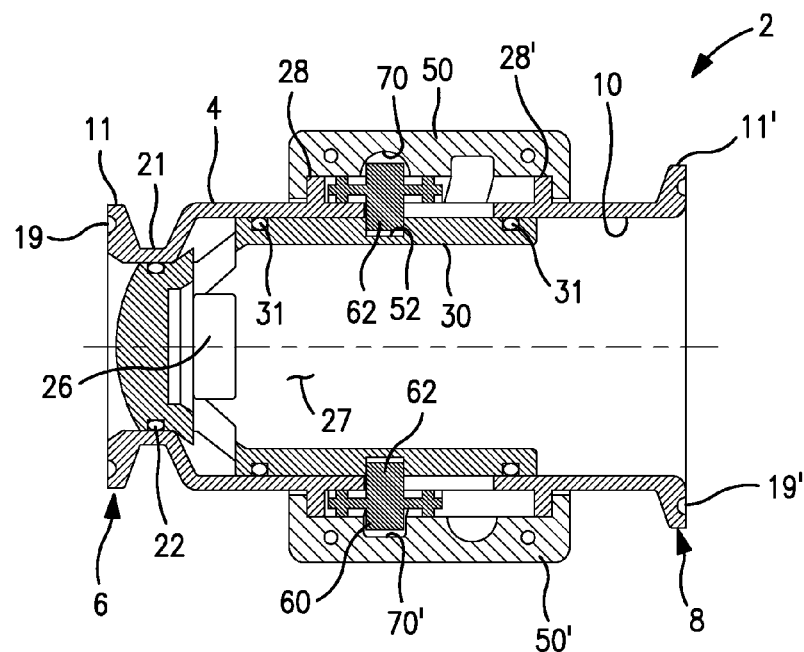
FIG. 1 is a cross-sectional view of a fluid transfer device shown in a closed position in accordance with certain embodiments.
Figure 2:
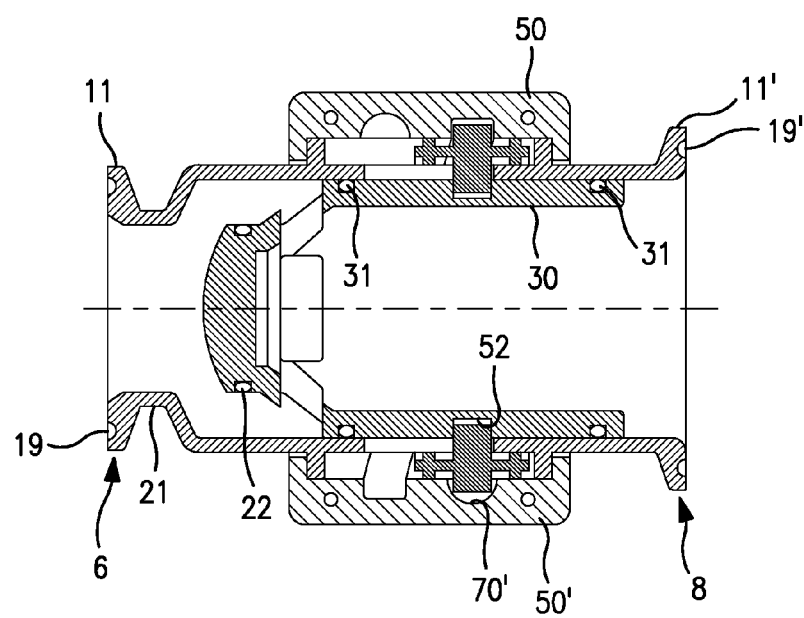
FIG. 2 is a cross-sectional view of a fluid transfer device shown in an open position in accordance with certain embodiments.
Figure 3:
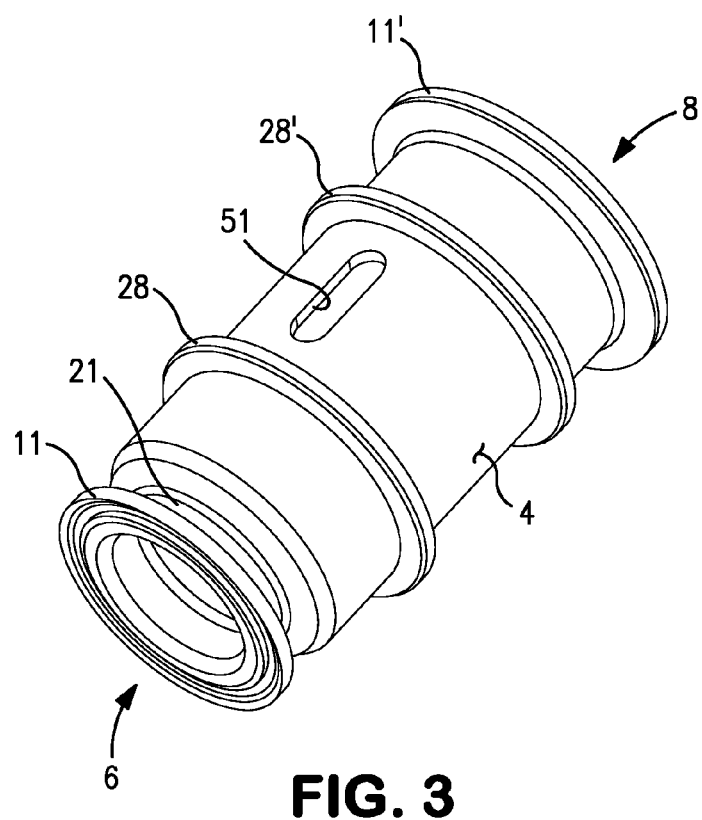
FIG. 3 is a perspective view of the body of a fluid transfer device in accordance with certain embodiments.

Turning now to FIGS. 1-3, the device 2 includes a body 4 having a first end 6 and a second end 8 spaced from the first end 6. The body 4 also has a bore 10 extending axially from the first end 6 to the second end 8. In certain embodiments, the bore 10 is generally circular in cross section. Preferably first end 6 has an annular flange 11 that extends radially outwardly. The front sealing face of the annular flange can include an annular groove 19 for receiving an O-ring or the like (not shown) to assist in sealing the front sealing face against the component it attaches to. Preferably second end 8 also has an annular flange 11' that also extends radially outwardly, and also can include a sealing face having an annular groove 19' for receiving an O-ring or the like (not shown). Preferably the internal diameter of the bore 10 is substantially constant except where it tapers to a smaller diameter defined by the annular wall 21 near the first end 6.

Spaced radially extending annular outer flanges 28, 28' are positioned on the outer wall of the body 4, as best seen in FIG. 3. These flanges function to position the cam actuator collars 50 as discussed in greater detail below. A pair of oppositely positioned cam slots 51, 51', preferably oval-shaped, are formed in the body 4, again as discussed in greater detail below.

Figure 4:
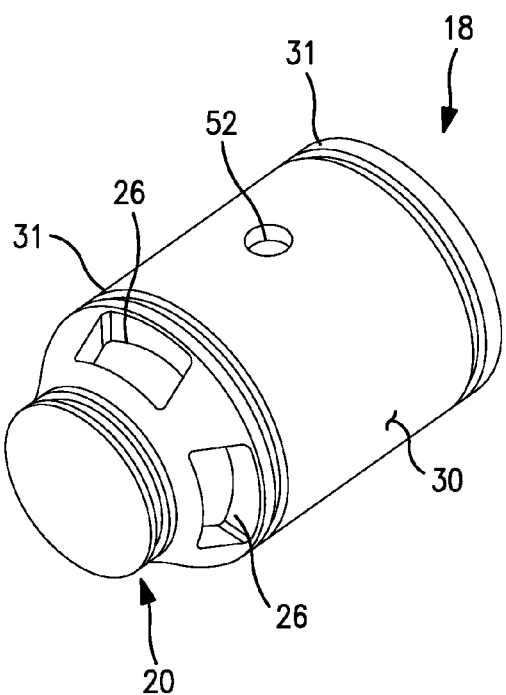
FIG. 4 is a perspective view of a plunger in accordance with certain embodiments.
Figure 4A:
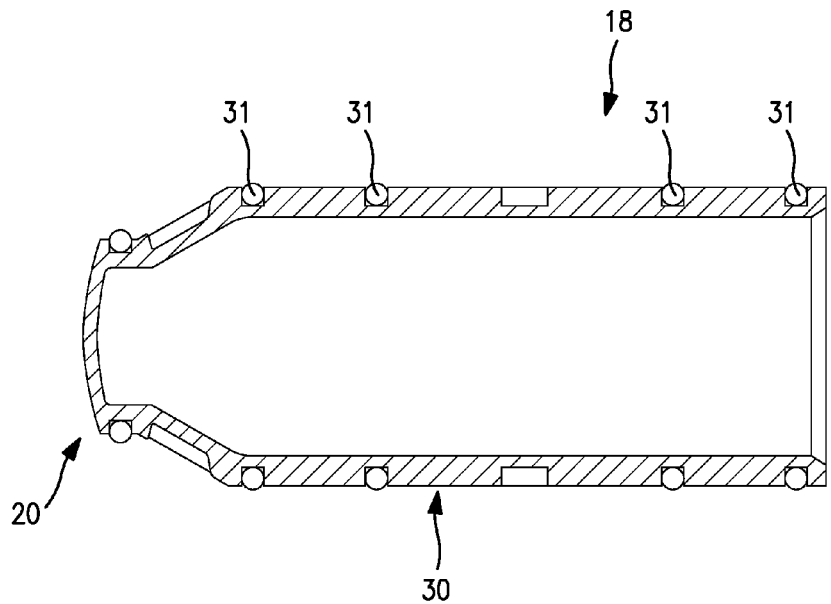
FIG. 4A is a cross-sectional view of a plunger in accordance with certain embodiments.

The bore 10 is configured to receive a plunger 18 (FIGS. 4, 4A). In certain embodiments, the plunger 18 is configured to slide within the bore 10 upon actuation, as discussed in greater detail below. Accordingly, in certain embodiments, the plunger has a generally circular cross section, with an outside diameter slightly smaller than the internal diameter of the bore 10 in the portion of the body where the plunger slides from a valve open to a valve closed position. The length of the cam slots 51, 51' in the axial direction can be used to set the distance the plunger 18 can travel within the bore 10 of the body 4. The main body portion 30 of the plunger can have one or more annular grooves 31 (two shown in FIG. 4) to receive an O-ring 31' or the like to assist in sealing the plunger 18 against the inner wall of the body 4 or also against bore 10. The sealing end 20 of the plunger 18 that extends axially from the main body portion 30 is shaped to seal against radially inwardly extending annular wall 21 of the bore 10, as best seen in FIG. 1. Thus, the internal diameter of bore 10 in the vicinity of annular wall 21 is less than the internal diameter of bore 10 elsewhere within the body 4. One or more O-rings 22 or the like can be placed in an annular groove in the sealing end 20 of the plunger 18 to effectuate a liquid tight seal against the annular wall 21. The plunger 18 contains one or more openings 26 as well as a fluid channel 27 that forms a fluid connection to a downstream component or tubing (not shown). Preferably the openings 26 are equally spaced around the circumference of the plunger 18, and are located in the tapering portion that connects the main body portion 30 to the sealing end 20, as shown. The main body portion includes oppositely positioned apertures 52, 52' as discussed in greater detail below.

FIG. 4A illustrates another embodiment of the plunger, denoted 18'. In the embodiment of FIG. 4A, additional sealing grooves are provided in the plunger body, which receive respective O-rings as shown, in order to improve sealing and thus separation of the non-sterile environment and the sterile internal volume of the fluid transfer device.

Figure 5:
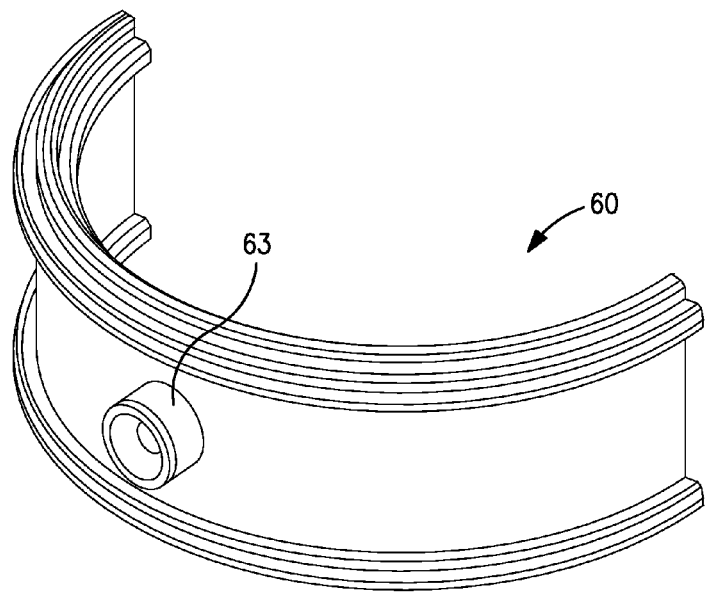
FIG. 5 is a perspective view of a split ring in accordance with certain embodiments.

Preferably the entire plunger 18 is contained within the bore 10 of the body 4, so that the length of the device 2 does not change regardless of whether the plunger is in the sealing position closing the valve (as seen in FIG. 1), or is on the fully open position opening the valve (as seen in FIG. 2). Accordingly, in accordance with certain embodiments, in order to actuate the plunger, a camming mechanism preferably is used. The camming mechanism includes a pair of split rings 60, 60', as seen in FIG. 5, and a pair of split cam actuator collars 50, 50', as seen in FIG. 6.

Each split ring 60, 60' is preferably identical, and includes a radially inwardly extending plunger engaging member 62, as seen in FIG. 1, and a radially outwardly extending cam actuator collar engaging member 63. In certain embodiments, the radially inwardly extending plunger engaging member 62 and the radially outwardly extending cam actuator collar engaging member 63 can be a single member that extends in both directions through an aperture in the split ring. Alternatively, two separate members can be formed on or attached to the split ring. Preferably the radially inwardly extending member 62 is a pin that is shaped to be received by aperture 52 on the plunger main body 30, as seen in FIGS. 1 and 2. Preferably the radially outwardly extending member 63 is a pin that is shaped to ride in a respective groove 70, 70' provided in each cam actuator collar.

Figure 6:
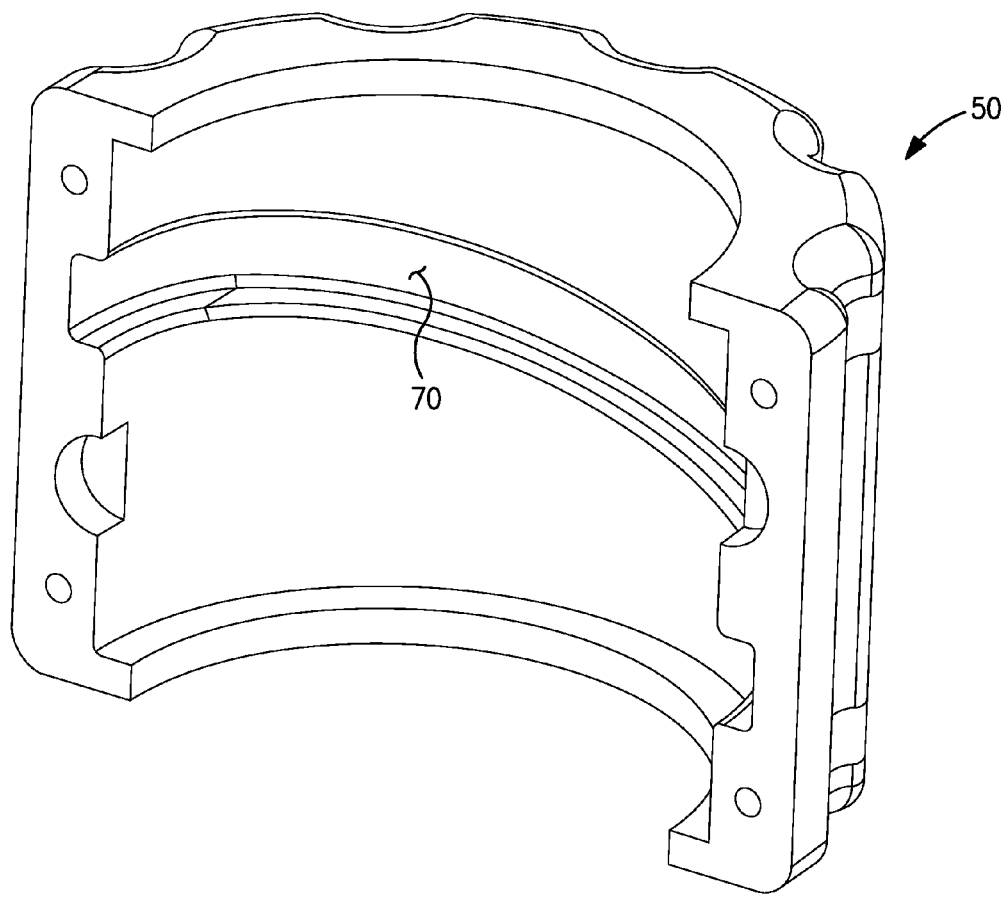
FIG. 6 is a perspective view of a collar half-ring in accordance with certain embodiments.

As shown in FIG. 6, each cam actuator collar preferably includes a knurled outer wall to assist in enabling the user to grasp and turn the collar by hand. The inner wall of each actuator collar is provided with a sloping groove 70 or 70', configured to receive in sliding relation, when in the assembled condition, the radially outwardly extending member 63 of a respective split ring collar 60, 60'.

In the assembled state, the plunger 18 is positioned in the bore 10 of the body 4, and each split ring collar 60, 60' is positioned about the outer circumference of the body 4 so that the radially inwardly extending members 62 protrude through a respective cam slot 51, 51' and are received by a corresponding aperture 52 in the plunger 18. As a result, axial movement of each split ring collar 60, 60' causes the radially inwardly extending member 62 to slide in its corresponding guidance slot 51 or 51', as the case may be, and due to the engagement of each of the members 62 in a plunger aperture 52, causes the plunger 18 to move axially as well.

Figure 7:
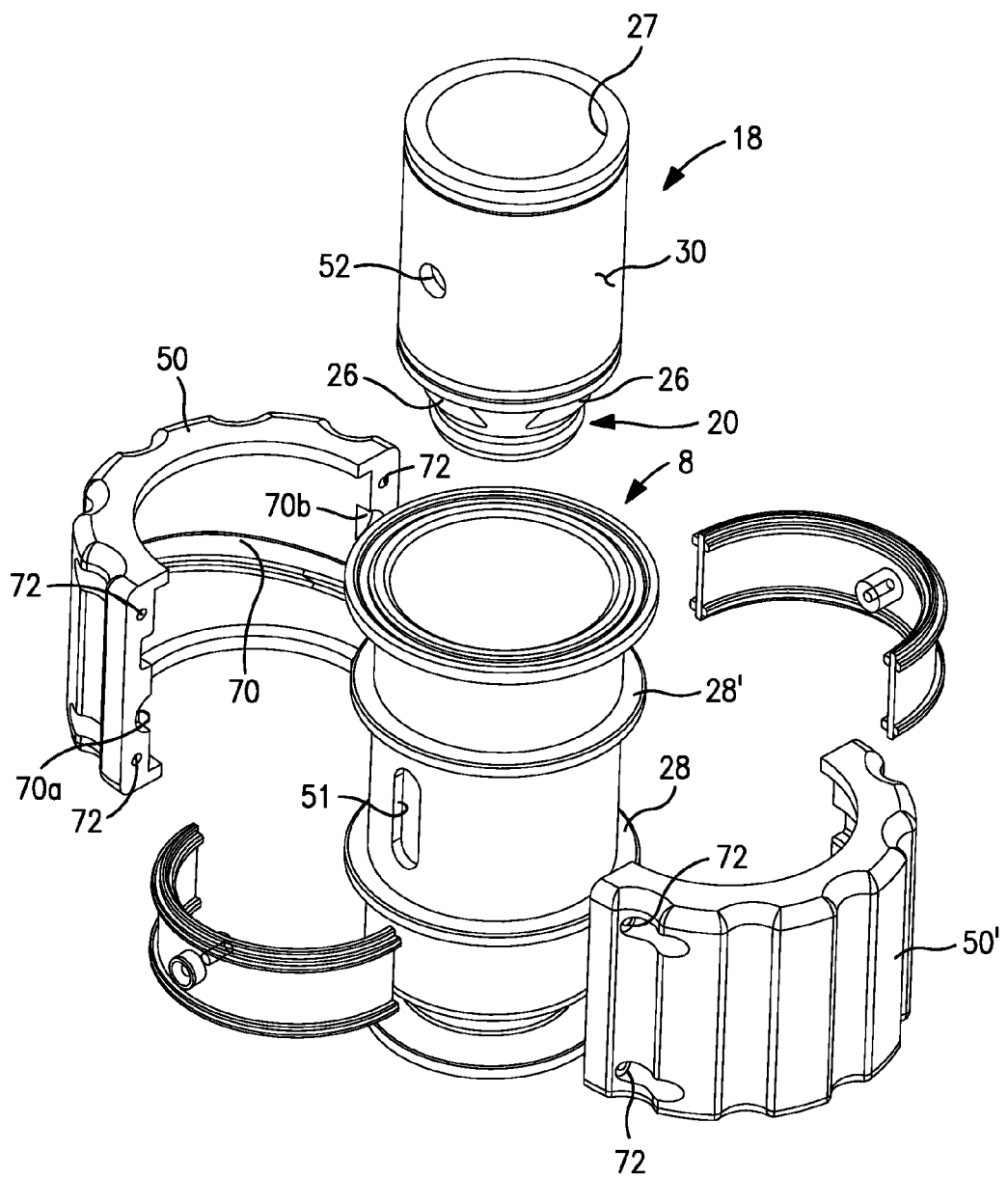
FIG. 7 is an exploded perspective view of a fluid transfer device in accordance with certain embodiments.

The cam actuator collars 50, 50' are fixed in place about the split ring collars 60, 60', such that the radially outwardly extending members 63 of each split ring collar are received in sliding relation by a respective groove 70, 70' in a cam actuator collar 50, 50'. As a result, rotation of the cam actuator collar causes the radially outwardly extending members 63 to ride in the groove 70, 70'. The cam actuator collars 50, 50' can be fixed in place by any suitable method, such as by providing apertures 72 in each collar and fixing the two collars together with screws. At least a portion of each groove 70, 70' is sloped with respect to horizontal, so that as the members 63 slide in the groove, there is an axial component to their movement as well. The extent of the slope, both in terms of its steepness and its length, thus can be used to limit the length of travel of the plunger 18 in the bore 10 of the body 4. For example, in certain embodiments the slope of the grooves 70, 70' can be gradual and constant, as shown in FIG. 6. In other embodiments, the grooves can have either a small or zero slope at and near the terminal ends of each collar 50, 50', and a relatively steep slope between the portions of the small or zero slope. The groove 70 in collar 50 is positioned so that when collar 50 and collar 50' are mated in the assembled condition, both ends of the groove 70 extend into the collar 50'. Similarly, the groove 70' in collar 50' is positioned so that when collar 50 and collar 50' are mated in the assembled condition, both ends of the groove 70' of collar 50' extend into the collar 50 (e.g., at 70a and 70b shown in FIG. 7).

Figure 10:
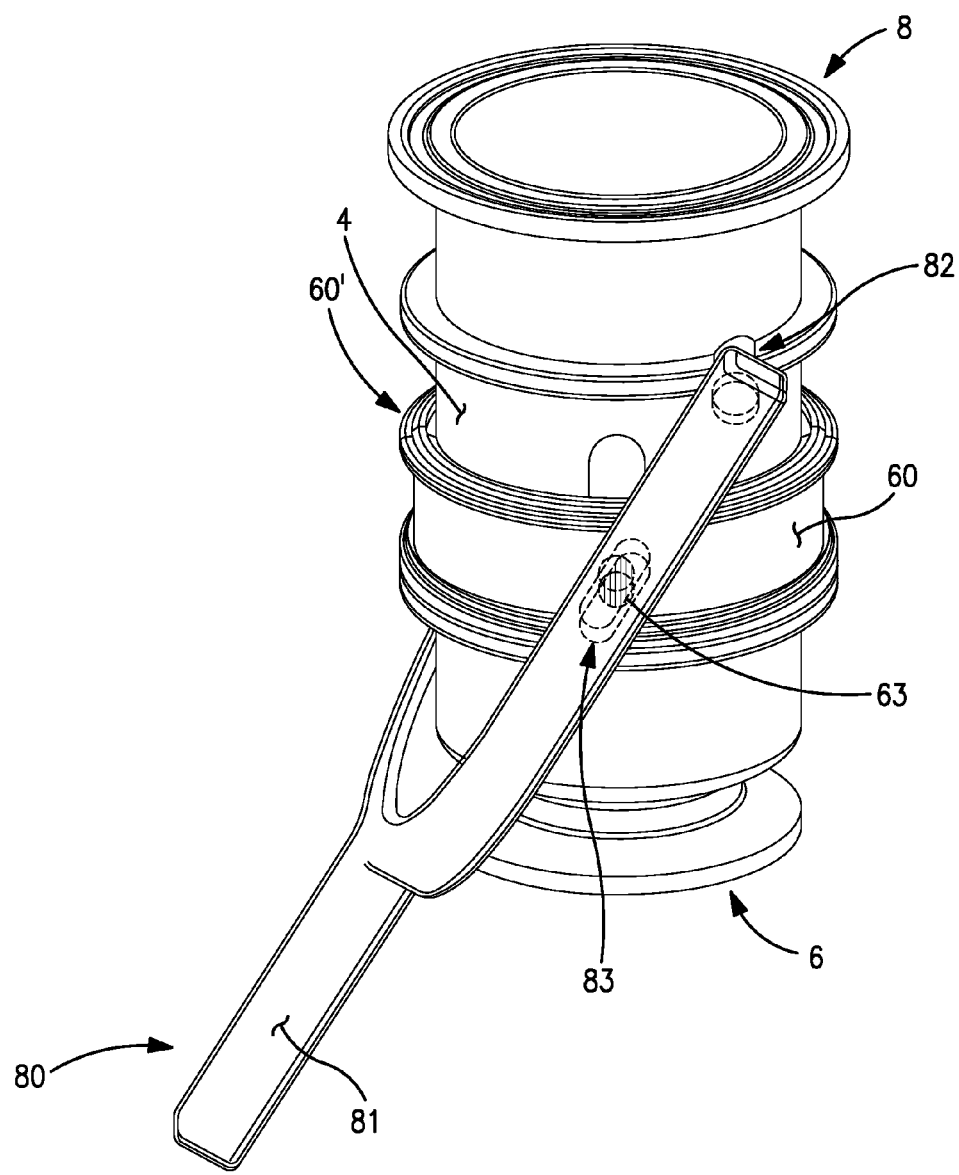
FIG. 10 is a perspective view of a fluid transfer device in accordance with certain embodiments.

In still further embodiments, a fork and pivot mechanism as shown in FIG. 10 can be used to engage and capture the split ring collars 60, 60', such that the overall lateral motion of the fork will cause the split ring collars to move lateral. The pivot of the fork 80 is connected to the body 4 such that as the fork handle 81 moves toward the first end 6 the fluid transfer devices moves into the closed position. To move the fluid transfer device the user moves the fork handle toward the second end 8. The fork can be fixed in place by any suitable method, such as by providing a counter bore in each tine of the fork which engage the oppositely arranged pivots 82 and 82' (not shown) and fixing the fork to the pivots such as with screws or the like. The pivots can be formed as details of the body 4 or separate pieces attached by other means such as welding or screws to body 4. At least a portion of each fork contains oppositely arranged grooves 83, 83' (only 83 shown) that give mechanical advantage to move the slip ring collars by engaging outwardly extending members 63 and 63' (only 63 shown, and shown hatched within the grooves). The extent of the slope of the groove, both in terms of its steepness and its length, thus can be used to limit the length of travel of the plunger 18 in the bore 10 of the body 4.

In alternative embodiments, the slip ring collars could be engaged to produce axial motion by the use of a rack and pinion system or a simple push-pull mechanism, although the mechanical advantage as described by the other embodiments disclosed herein would not be present.

In certain embodiments, the device 2 can be attached to an upstream component or pipe by sanitary flange 11 formed as part of the body 4. The flange 11 can be attached to the upstream component or pipe by a clamp such as a Tri-Clover™ fitting, Ladish™ fitting, ClickClamp™ clamp or the like. Sterilization, such as steam treatment, can be used to sterilize the interface where necessary or desirable.

In certain embodiments, means may be provided enabling the user to determine if the fluid transfer device is in the open or closed position. Although visual alignment marks are common to other devices, such as the Lynx ST® connector, other embodiments improve on that means. One such embodiment is the use of multicolored components such that the slip ring collar 60 is chosen from a visual notable color and the cam actuator collar 50 has a hole or transparent window collocated with the end of the groove 70, for instance 70a. When the fluid transfer device is in its fully closed position, the color of 60' will show through the cam actuator collar 50.

The position also may be determined through electronic means whereby an electronic sensor engages a sensor reader. A RFID tag can be positioned within an axially moving component, such as sealing end 20. A RFID reader located outside the fluid transfer device can then be used to detect a signal from the RFID tag when it is within range. The signal can be indicative of the relative position of the movable component.

By providing the fluid transfer device on inlet and outlet ports of filter capsules, improved means of manifolding or configuring the capsules to the user's requirements are achieved. Of particular note is the reduction of custom piping that interconnects multiple filter capsules without the need for external manifold piping. For example, as shown in FIG. 9, feed (91 and 91') and permeate (92 and 92') fluid transfer devices, can be integrated in two co-axial orientations (94 and 93, respectively) with a common plane, 95. This embodiment improves the connection methods within an existing assembly and the assembly of capsules can be slid into and out of place from any perpendicular axis, for example 96, to the axis of the flow stream (97).

Figure 8A:
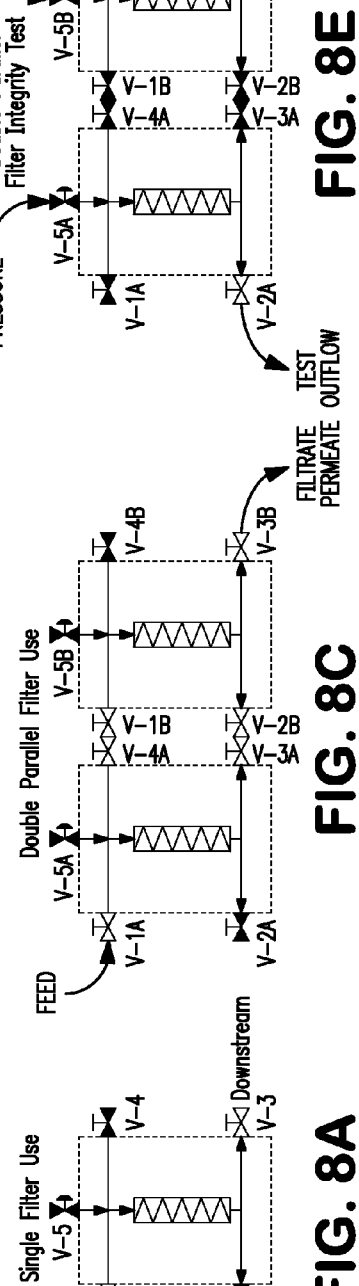
FIGS. 8A-8F are schematic diagrams of multiple filter capsules connected in different configurations with fluid transfer devices in accordance with certain embodiments.
Figure 8B:
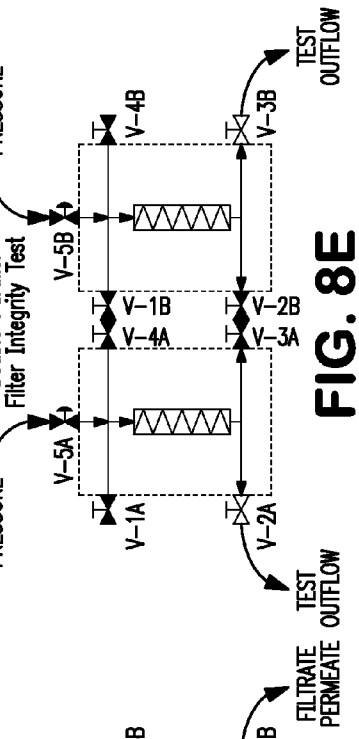
Figure 8C:
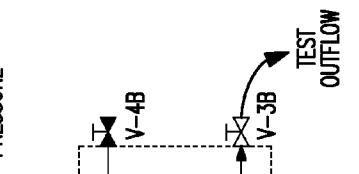

In a parallel configuration of capsule filters, upstream feeds 94 are connected together, producing a common feed line, as shown in FIG. 8C. Before processing and during the installation of the filters into the users system, all the fluid transfer devices remain closed (shown as black-out). A user desiring a parallel configuration of filters would assembly them as shown in FIG. 8C. A user may choose a parallel configuration to improve the overall filtrate capacity of the process or achieve other process improvements. During installation the single feed will connect to the fluid transfer device V-1A and the user's single filtrate permeate will connect to the fluid transfer device V-3B to the user's permeate line. During processing the fluid transfer devices are opened (shown as white-out) such that the intended filtrate will flow through V-1A across the left filter surface as well as flow out V-4A and into the second filter via V-1B in fluid communication with V-4A. Once the intended filtrate fills the upstream volume before the filter surface, the filtrate will flow across both filter surfaces and exit the two capsules. The two fluid transfer devices, V-2A and V-4B, remain closed (shown as black-out) in this configuration, forcing the filtrate out V-3A into V-2B (in fluid communication with V-3A) and equally out V-3B into the user's single permeate line. In other configurations of open and closed fluid transfer devices, the user can improve their process. With the fluid transfer devices integrated with the filter capsules the user can choose to manifold them together to form a parallel configuration of sufficient capsule filters without the need to fabricate custom manifolds. Other embodiments are within the scope of the present invention.

Figure 8D:
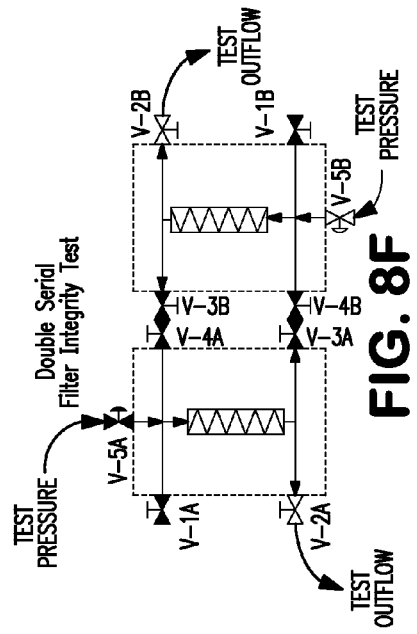

In a serial configuration of capsule filters, as shown in FIG. 8D, a user can perform a double filtration, such that the intended filtrate is passed through two similar or dissimilar filters, which reduces the risk of a contamination due to the breach of a single filter, or other such desired processing conditions. Before processing and during installation all the fluid transfer devices remain closed. The user's feed line is connected to V-1A and filtrate permeate line is connected to V-2B. The second filter device is oriented by placing its feed fluid transfer device, V-4B, in fluid communication with the permeate fluid transfer device V-3A of the first filter. During processing certain fluid transfer devices remain closed such that the intended filtrate enters V-1A flowing across the filter surface and exits the first filter via V-3A and enters the second filter into V-4B in view of the fluid communication therebetween. The intended filtrate then continues to flow across the second filter surface and exits V-2B. Other configurations whereby the fluid transfer devices are opened and closed with the serial configuration allow users to simplify their processing. Other embodiments are within the scope of the present invention.

Once the fluid transfer device(s) are assembled to the capsule filter(s), the devices can be closed and terminally sterilized such as by gamma radiation by the manufacturer and supplied sterile to the user. In this condition the user will receive a pre-sterilized capsule filter which is ready for installation and use. Some filter capsules, such as Opticap® units from Millipore, do not have integrated fluid transfer devices. During installation and processing these filters must be sterilized before the intended filtrate is introduced. The user may assembly them to their system and autoclave the system or perform a steam in place (SIP). Autoclaving the whole assembled system requires significant time and the assembly is complicated to transport in and out of the autoclave. If a user chooses to perform a SIP, the filter must be chosen such that it will safely survive the high temperature and pressure for the full length of processing time. Because the embodiments disclosed herein allow the isolation of the SIP conditions from the inside of the capsule, the materials of construction within the core can be chosen differently and from a family that are more appropriate for cost, weight, or fabrication considerations. For example, Opticap® filters are sold in two types. One type is constructed of materials that will survive gamma sterilization but not SIP conditions. The other can survive SIP and autoclave conditions but breaks down during gamma sterilization. In accordance with certain embodiments, the fluid transfer devices can be constructed out of material that survives autoclave, SIP, and gamma sterilization and the inside of the filter is chosen of more economical materials such as polyester, nylon, or other such low cost thermoplastics. During installation and any subsequent steam sterilization process, the device(s) will remain closed, maintaining sterility. After sterilization, the valves can be opened, exposing the inside of the capsule(s) to the process stream.

The embodiments disclosed herein also allow for improved integrity testing on the configured filter capsules. Integrity testing commonly involves determining if the test results meet the test specifications. For example, it is common within the industry to perform an air diffusion flow rate test to determine if a filter is integral. If the flow rate is greater than the test specification, the filter is deemed non-integral as the defect is adding an incremental flow. As one skilled in the art of integrity testing can demonstrate that the larger the number of filters that are assembled to a common test port, the greater the error simply due to the larger natural filter manufacturing variation and the thermodynamic effects of a larger housing. The embodiments disclosed herein allow for the isolation of individual filter capsules, thereby improving the integrity testing method.

For example, a typical single filter use configuration is shown in FIG. 8A, and the state of the various transfer devices for integrity testing is shown in the simple configuration of FIG. 8B, where the integrity test pressure can be connected to the fluid transfer device V-5. During testing the other fluid transfer devices remain closed, except for V-3. Although this is a preferred arrangement, other configurations can be chosen by the user without rearranging the plumbing or connections to the capsule filter.

Figure 8E:
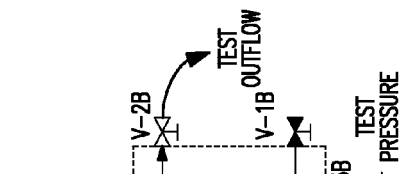
Figure 8F:
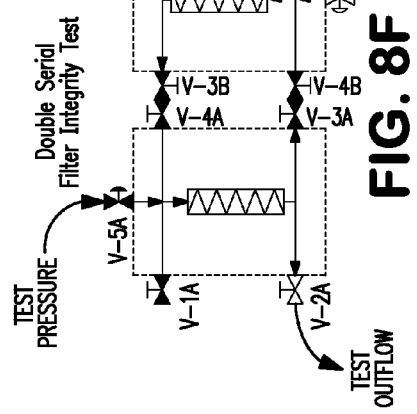

To perform an integrity testing of multiple filters in either a parallel and serial configuration, shown in FIGS. 8E and 8F respectively, the testing pressure is connected to an additional fluid transfer device. This additional fluid transfer device allows the user to retain the original fluid connections while executing a test. A typical filter, such as Opticap® filters from Millipore, do not have isolation valves and require the user to perform the integrity test on all the connected filters together. A small leak will be hidden within the additive flow of all the filters. However, capsule filters with integrated fluid transfer devices allow the user to isolate each filter capsule from another during the test reducing the total gas flow in relation to any background leaks. Of particular note, the embodiments disclosed herein allow the filters to be tested in their processing configuration which will indicate if there are any leaks related to the fluid interconnections. Although a common test method is known as pressure hold using a closed high pressure, other test methods can be employed. For instance, in a parallel configuration similar to that shown in FIG. 8C, the test pressure is connected to V-5A with V-1A, V-2A, V-4B, and V-3B being closed. The user may open V-4A, V-1B, V-3A, and V-2B whereby the test pressure challenges the interconnection points between the capsules. This allows the user to perform a housing test whereby any change in the test pressure indicates a leak at the interconnection points.

The method of integrity testing a set of capsule filters with integrated fluid transfer devices that are configured in a serial flow path, as shown in 8F, is described here. The test pressure is connected to V-5A with V-4A and V-3A closed and V-2A open. As the integrity test proceeds, the flow is measured at the outlet of V-2A whereby the integrity of the left filter can be determined. However, as is common with existing filters, the right-hand filter, which is considered downstream, cannot be tested distinctly from the left without measuring flow from V-2B. It is notable that the embodiments disclosed herein allow the user new methods to perform an integrity test of both filters in a serial connection without disturbing the sterile fluid pathway that was established at the beginning of processing. For example, in the serial processing configuration of FIG. 8D, the user's fluid enters V-1A and exits V-2B, with the other fluid transfer devices in the states as shown. Although both areas adjacent to these fluid transfer devices need to be sterile, it is advantageous to perform an integrity test of the two filters whereby the sterility downstream of V-2B remains integral and undisturbed. Commonly capsule filters without fluid transfer devices require the detachment of the downstream fluid connection to measure actual gas flow. However, the embodiments disclosed herein allow the user to perform an integrity test using actual gas flow by using V-5A. In this embodiment, the two filters are arranged serially as in FIG. 8F for processing. To test the right-hand filter, the test pressure is attached to V-5B with V-1B, V-4B, V-2B, V-1A, and V-2A, V-3A closed (not shown in this configuration). The test gas will flow through the right membrane surface and through the open V-3B, V-4A and to V-5A. The actual gas flow can be measured at V-5A.

Although these embodiments describe integrity testing using actual gas flow the disclosed embodiments are advantageous to integrity testing that is done by pressure hold. Each capsule filter can be isolated from the others through closing the interconnecting fluid transfer devices.

What is claimed is:

1. A valve having an axial length, comprising:
 a body having:
  a first end containing a face configured to be attached to an upstream component;
  a second end configured to be attached to a downstream component; and
  a bore extending axially from the first end to the second end;
 a plunger axially movable within said bore between an open position and a closed position, the plunger having a first end and a second end; and
 an actuator operatively connected to the plunger by a pair of split rings, each split ring including a radially inwardly extending plunger engaging member and a radially outwardly extending actuator engaging member operatively connecting the actuator and the plunger, such that rotational movement of the actuator causes the plunger to move axially between the open and closed positions without altering the axial length of the valve,
 wherein:
  the valve is in the closed position when the first end of the plunger is in alignment with the face of the body; and
  the first end of the plunger being in alignment with the face of the body forms a steamable surface and a sterile barrier against the environment to a remainder of the interior of the bore, the plunger and a downstream component.

2. The valve of claim 1, wherein the actuator is a split ring actuator, each split ring of the actuator having a sloped groove and a groove end for receiving the radially outwardly extending actuator engaging members in sliding relation, such that, when the split ring actuator is assembled, each radially outwardly extending actuator engaging member rides in the sloped groove of one split ring of the actuator and the groove end of the opposing split ring of the actuator.

3. The valve of claim 2, wherein the body further comprises spaced radially extending annular outer flanges positioned on an outer wall of the body, and each split ring of the actuator further includes radially inwardly extending protrusions, a length of the actuator protrusions and a length of the body flanges being in contact with one another.

4. The valve of claim 1, wherein each split ring further includes a first and a second split ring collar shaped to ride against an outer wall of the body and an interior surface of the actuator.

5. The valve of claim 4, wherein the radially inwardly extending plunger engaging member and the radially outwardly extending actuator engaging member are positioned between the first and the second split ring collars.

6. A manifold assembly unit, comprising a filter capsule having a feed port and a permeate port, a pair of valves in fluid communication with the feed port and a pair of valves in fluid communication with the permeate port, wherein each valve has an axial length and independently comprises:
 a body having:
  a first end containing a face designed to be attached to an upstream component, a downstream component or a second manifold assembly unit,
  a second end attached to the filter capsule, and
  a bore extending axially from the first end to the second end;
 a plunger axially movable within said bore between an open position and a closed position, the plunger having a first end and a second end; and
 an actuator operatively connected to the plunger such that movement of the actuator causes the plunger to move axially between the open and closed positions without altering the axial length of the valve,
 wherein:
  the valve is in the closed position when the first end of the plunger is in alignment with the face of the body, and
  the first end of the plunger being in alignment with the face of the body forms a steamable surface and a sterile barrier against the environment to a remainder of the interior of the bore, the plunger and the filter capsule.

7. The manifold assembly unit of claim 6, wherein the valves in fluid communication with the feed port are coaxially aligned.

8. The manifold assembly unit of claim 6, wherein the valves in fluid communication with the permeate port are coaxially aligned.

9. The manifold assembly unit of claim 6, wherein the valves in fluid communication with the feed port are coaxially aligned and the valves in fluid communication with the permeate port are coaxially aligned in a common plane.

10. A manifold assembly comprising at least two of the manifold assembly units of claim 6 in fluid communication.

11. The manifold assembly of claim 10, wherein the at least two manifold assembly units are connected in a parallel configuration.

12. The manifold assembly of claim 10, wherein the at least two manifold assembly units are connected in a serial configuration.

* * * * *